United States Patent
Fifolt et al.

(10) Patent No.: US 6,201,152 B1
(45) Date of Patent: Mar. 13, 2001

(54) METHOD OF MAKING 3,5-DICHLORO-P-TOLUOYL CHLORIDE

(75) Inventors: Michael J. Fifolt; Sanjay Mandal; William S. Derwin, all of Grand Island, NY (US)

(73) Assignee: Occidental Chemical Corporation, Dallas, TX (US)

( * ) Notice: Subject to any disclaimer, the term of this patent is extended or adjusted under 35 U.S.C. 154(b) by 0 days.

(21) Appl. No.: 09/434,630

(22) Filed: Nov. 5, 1999

(51) Int. Cl.$^7$ ............................... C07C 51/58
(52) U.S. Cl. ............................................. 562/861
(58) Field of Search ............................... 562/861

(56) References Cited

U.S. PATENT DOCUMENTS 4,080,378   3/1978   Zoche et al. .

*Primary Examiner*—Paul J. Killos
(74) *Attorney, Agent, or Firm*—Richard D. Fuerle; Anne E. Brookes

(57) ABSTRACT

Disclosed is a method of making 3,5-dichloro-p-toluoyl chloride. A mixture is prepared of methyl-3,5-dichloro-4-methylbenzoate, about 1 to about 1.4 equivalents of an α,α,α-trichloromethylbenzene, and about 0.01 to about 0.2 equivalents of a catalyst selected from the group consisting of ammonium septamolybdate, ammonium dimolybdate, and mixtures thereof. The mixture is heated to a temperature of about 150 to about 180° C.

16 Claims, No Drawings

METHOD OF MAKING 3,5-DICHLORO-P-TOLUOYL CHLORIDE

BACKGROUND OF THE INVENTION

This invention relates to a method of making 3,5-dichloro-p-toluoyl chloride ("DCTOC," also called "3,5-dichloro-4-methylbenzoyl chloride") by reacting 3,5-dichloromethyltoluate ("DCMT," also called "methyl-3,5-dichloro-4-methylbenzoate") with an α,α,α-trichloromethylbenzene. In particular, it relates to the use of ammonium septamolybdate, $(NH_4)_6Mo_7O_{24}\cdot 4H_2O$ (ASM), or ammonium dimolybdate, $(NH_4)_2Mo_2O_7\cdot 2H_2O$ (ADM), as the catalyst in that reaction. (The amounts of water of hydration may vary.)

In U.S. Pat. No. 4,080,378 toluoyl chloride is made by reacting p-toluylic acid methyl ester with 1,4-bis-(trichloromethyl)-benzene and p-chlorobenzoyl chloride is made by reacting p-chlorobenzoic acid methyl ester with p-chlorobenzotrichloride. In both reactions, the catalyst is molybdenum trioxide $(MoO_3)$.

SUMMARY OF THE INVENTION

We have discovered that DCTOC can be made by reacting DCMT with an α,α,α-trichloromethylbenzene at conversions of 99% and 96% if the catalyst is ASM or ADM, respectively. It is surprising that such high conversions can be achieved with these catalysts because closely related molybdenum catalysts, such as molybdenum trioxide, have much lower conversions.

DESCRIPTION OF THE PREFERRED EMBODIMENTS

In this invention DCTOC is made by reacting DCMT with an α,α,α-trichloromethylbenzene in the presence of a catalyst such as ASM, ADM, or a mixture thereof.

Examples of α,α,α-trichloromethylbenzenes that can be used include benzotrichloride (BTC), o-chlorobenzotrichloride, m-chlorobenzotrichloride, p-chlorobenzotrichloride (PCBTC), m-bis(trichloromethyl)benzene, p-bis(trichloromethyl)benzene 1,3-bis(trichloromethyl)-5-chlorobenzene, bis(trichloromethyl) dichlorobenzenes, and o-dichloromethyltrichloromethylbenzene. The preferred α,α,α-trichlormethylbenzenes are BTC and PCBTC as they are less expensive and the resulting coproduct (benzoyl chloride or p-chlorobenzoyl chloride, respectively) is commercially valuable. The amount of α,α,α-trichloromethylbenzene used should be about 1 to about 1.4 equivalents as less will leave unreacted DCMT and more may result in the production of unwanted byproducts. Preferably, about 1 to about 1.1 equivalents of the α,α,α-trichloromethylbenzene are used.

The amount of catalyst used should be about 0.01 to about 0.2 equivalents as less will result in a slower reaction and more is unnecessary and wasteful. The preferred amount of catalyst is about 0.02 to about 0.08 equivalents.

The general procedure is to charge the reactor with the DCMT, the α,α,α-trichloromethylbenzene, and the catalyst and heat the mixture to about 150 to about 180° C.; the reaction is slower at lower temperatures and at higher temperatures unwanted byproducts may be produced. The preferred temperature is about 155 to about 165° C. No solvent is needed for the reaction. The reaction is usually complete in about 5 to about 12 hours. The product mixture contains DCTOC and a benzoyl chloride, which can be separated by distillation. DCTOC is used as an agricultural intermediate, benzoyl chloride is used to make plasticizers and peroxides, and methyl chloride is a valuable gas.

The following examples further illustrate this invention.

EXAMPLE 1

Comparative

Into a reaction vessel was placed 28 g DCMT, 25.3 g BTC, and 79 mg molybdenum trioxide. The mixture was heated at 164° C. and followed by gas chromatography (GC). The reaction started very rapidly, but after 4.5 hours it stopped and an additional 79 mg of molybdenum trioxide had to be added to complete it. After a total of 11.25 hours the reaction mixture became thick and was stopped. The reaction mixture contained 53 wt % DCTOC, 37 wt % benzoyl chloride, 0 wt % BTC and 8 wt % DCMT. The following table shows the progress of the reaction:

| Time (hours) | $MoO_3$ (mole %) | % Conversion to 3,5-DCTOC (GC area %) | Incremental Reaction Rate (per hour) |
|---|---|---|---|
| 1 | 0.5 | 25 | 25 |
| 2 | 0.5 | 39 | 14 |
| 2.5 | 0.5 | 49 | 20 |
| 4.5 | 0.5 | 55 | 3 |
| 6 | 1.0 | 77 | 15 |
| 7 | 1.0 | 79 | 2 |
| 10.5 | 1.0 | 85 | 2 |

EXAMPLE 2

Example 1 was repeated using 12 DCMT, 10 g BTC, and 82 mg ADM. After 9 hours an additional 2 g BTC was added. After a total of ten hours the reaction was complete. The reaction mixture contained 43 wt % DCTOC, 36 wt % benzoyl chloride, 18 wt % BTC and 2 wt % DCMT. The following table shows the progress of the reaction:

| Time (hours) | ADM (mole %) | % Conversion to 3,5-DCTOC (GC area %) | Incremental Reaction Rate (per hour) |
|---|---|---|---|
| 1 | 0.5 | 0.23 | 0.23 |
| 2 | 0.5 | 0.24 | 0.02 |
| 3 | 0.5 | 0.24 | 0 |
| 4 | 0.5 | 0.31 | 0.07 |
| 5 | 0.5 | 6 | 6 |
| 6 | 0.5 | 16 | 10 |
| 7 | 0.5 | 35 | 19 |
| 8 | 0.5 | 63 | 27 |
| 9 | 0.5 | 80 | 17 |
| 10 | 0.5 | 96 | 16 |

EXAMPLE 3

Example 2 was repeated using 290 mg ASM and a temperature of 162° C. After ten hours the reaction was complete. The reaction mixture contained 53 wt % DCTC and 43 wt % benzoyl chloride. The following table shows the progress of the reaction:

| Time (hours) | ASM (mole %) | % Conversion to 3,5-DCTOC (GC area %) | Incremental Reaction Rate (per hour) |
|---|---|---|---|
| 1 | 0.5 | 6 | 6 |
| 2 | 0.5 | 10 | 4 |
| 3 | 0.5 | 17 | 7 |
| 4 | 0.5 | 47 | 30 |
| 5 | 0.5 | 85 | 38 |
| 6 | 0.5 | 88 | 3 |
| 7 | 0.5 | 90 | 2 |
| 8 | 0.5 | 91 | 1 |
| 9 | 0.5 | 92 | 1 |
| 10 | 0.5 | 100 | 8* |

*Additional 2 g BTC added.

In these Examples, when molybdenum trioxide was used the reaction was initially rapid but stopped until additional catalyst was added; when either ADM or ASM was used, the reaction started slowly, then accelerated to completion without the need for additional catalyst. This suggests that the catalytic mechanism of molybdenum trioxide is not the same as the catalytic mechanism of ADM and ASM.

We claim:

1. A method of making 3,5-dichloro-p-tolouyl chloride comprising
   (A) preparing a mixture of
      (1) methyl-3,5-dichloro-4-methylbenzoate;
      (2) about 1 to about 1.4 equivalents of an α,α,α-trichloromethylbenzene; and
      (3) about 0.01 to about 0.2 equivalents of a catalyst selected from the group consisting of ammonium septamolybdate, ammonium dimolybdate, and mixtures thereof; and
   (B) heating said mixture to a temperature of about 150 to about 180° C.

2. A method according to claim 1 wherein said catalyst is ammonium septamolybdate.

3. A method according to claim 1 wherein said catalyst is ammonium dimolybdate.

4. A method according to claim 1 wherein said α,α,α-trichloromethylbenzene is selected from the group consisting of benzotrichloride, o-chlorobenzotrichloride, m-chlorobenzotrichloride, p-chlorobenzotrichloride, m-bis(trichloromethyl)benzene, p-bis(trichloromethyl)benzene, 1,3-bis(trichloromethyl)-5-chlorobenzene, bis(trichloromethyl)dichlorobenzenes, and o-dichloromethyltrichloromethylbenzene.

5. A method according to claim 1 wherein said α,α,α-trichloromethylbenzene is benzotrichloride.

6. A method according to claim 1 wherein said α,α,α-trichloromethylbenzene is p-chlorobenzotrichloride.

7. A method according to claim 1 wherein said temperature is about 155 to about 165° C.

8. A method according to claim 1 wherein the amount of said catalyst is about 0.02 to about 0.08 equivalents.

9. A method according to claim 1 wherein the amount of said α,α,α-trichloromethylbenzene is about 1 to about 1.1 equivalents.

10. A method according to claim 1 including the additional last step of distilling the product mixture.

11. A method of making 3,5-dichloro-p-toluoyl chloride comprising
    (A) preparing a mixture of
       (1) methyl-3,5-dichloro-4-methylbenzoate;
       (2) about 1 to about 1.1 equivalents of an α,α,α-trichloromethylbenzene selected from the group consisting of benzotrichloride, p-chlorobenzotrichloride, and mixtures thereof; and
       (3) about 0.02 to about 0.08 equivalents of a catalyst of ammonium septamolybdate; and
    (B) heating said mixture to a temperature of about 155 to about 165° C.

12. A method according to claim 11 wherein said α,α,α-trichloromethylbenzene is benzotrichloride.

13. A method according to claim 11 wherein said α,α,α-trichloromethylbenzene is p-chlorobenzotrichloride.

14. A method of making 3,5-dichloro-p-toluoyl chloride comprising
    (A) preparing a mixture of
       (1) methyl-3,5-dichloro-4-methylbenzoate;
       (2) about 1 to about 1.1 equivalents of an α,α,α-trichloromethylbenzene selected from the group consisting of benzotrichloride, p-chlorobenzotrichloride, and mixtures thereof; and
       (3) about 0.02 to about 0.08 equivalents of a catalyst of ammonium dimolybdate; and
    (B) heating said mixture to a temperature of about 155 to about 165° C.

15. A method according to claim 14 wherein said α,α,α-trichloromethylbenzene is benzotrichloride.

16. A method according to claim 14 wherein said α,α,α-trichloromethylbenzene is p-chlorobenzotrichloride.

* * * * *